United States Patent [19]

Stolar

[11] Patent Number: 4,470,978
[45] Date of Patent: Sep. 11, 1984

[54] SYNERGISTIC ANTIBACTERIAL COMPOSITION

[75] Inventor: Maurice E. Stolar, Tel-Aviv, Israel

[73] Assignee: Abic Ltd., Israel

[21] Appl. No.: 427,891

[22] Filed: Sep. 28, 1982

Related U.S. Application Data

[63] Continuation-in-part of Ser. No. 214,736, Dec. 9, 1980, abandoned, which is a continuation of Ser. No. 059,382, Jul. 20, 1979, abandoned.

[30] Foreign Application Priority Data

Jul. 25, 1978 [IL] Israel ..................................... 55214

[51] Int. Cl.³ .................. A61K 31/625; A61K 31/63; A61K 31/505; A61K 31/085
[52] U.S. Cl. .................................... 424/229; 424/228; 424/251; 424/340
[58] Field of Search ........................ 424/229, 251, 340

[56] References Cited

FOREIGN PATENT DOCUMENTS 1583994 12/1969 France .

OTHER PUBLICATIONS

Chemical Abstracts, 69:74706f (1968).
Chemical Abstracts, 77:14793n (1972).
PDR, 27 ed., 1973, pp. 918 and 919.

Primary Examiner—Jerome D. Goldberg
Attorney, Agent, or Firm—Steinberg & Raskin

[57] ABSTRACT

A composition is prepared of trimethoprim, an antibacterial sulfa drug or a pharmaceutically acceptable salt thereof, and phenoxyethanol in synergistically effective and antibacterial effective amounts thereof. Preferably the ratio of trimethoprim to sulfa drug to phenoxyethanol is between about 1:3–10:0.1–0.6.

7 Claims, No Drawings

SYNERGISTIC ANTIBACTERIAL COMPOSITION

CROSS REFERENCE TO RELATED APPLICATIONS

This application is a continuation in part of my copending application Ser. No. 214,736, filed Dec. 9, 1980, for "Antibacterial Composition", now abandoned, which in turn is a continuation of application Ser. No. 059,382 filed July 20, 1979, for "Antibacterial Composition", now abandoned.

BACKGROUND OF THE INVENTION

Sulfa drugs are known to have a good antibacterial activity. The compound 2, 4-diamino-5-(3, 4, 5-trimethoxy benzyl)pyrimidine (hereinafter referred to as "trimethoprim") is also known to have good antibacterial activity.

Still further, it is known that when sulfa drugs are mixed with trimethoprim in a ratio of trimethoprim to sulfa drug of 10:1-5:1, a synergistic action is observed.

Attempts are, however, constantly being made to improve the antibacterial activity of such drugs.

SUMMARY OF THE INVENTION

In accordance with the present invention a synergistic composition is provided of trimethoprim, an antibacterial sulfa drug or a pharmaceutically acceptable salt thereof, and phenoxyethanol.

It is a primary object of the present invention to provide improved antibacterial activity for sulfa drugs and trimethoprim.

It is yet a further object of the present invention to provide for compositions of trimethoprim, sulfa drug and phenoxyethanol which compositions have synergistic activity far greater than the activity resulting from the sum of the component parts thereof.

Other objects and advantages of the present invention will be apparent from a further reading of the specification and of the appended claims.

With the above and other objects in view, the present invention mainly comprises an antibacterial pharmaceutical composition for internal administration, comprising synergistically effective amounts of phenoxyethanol, trimethoprim and an antibacterial sulfa drug or a pharmaceutically acceptable salt thereof in an antibacterial effective amount, the phenoxyethanol, trimethoprim and sulfa drug or salt thereof being distributed in a pharmaceutically acceptable carrier suitable for internal administration.

In accordance with the preferred embodiment of the present invention, the proportions of trimethoprim to sulfa drug to phenoxyethanol are preferably in the range of 1:3-10:0.1-0.6.

It has surprisingly been found that when phenoxyethanol is added to a mixture of a sulfa drug and trimethoprim that the synergistic activity of the overall composition is increased to an unexpected extent. This is most surprising in view of the fact that when phenoxyethanol is added to either the sulfa drug alone or the trimethoprim alone, no such activity is observed.

Still further, if the trimethoprim is replaced by any other diaminopyrimidine, such as pyrimethamine, the increased activity is not achieved.

It is preferred according to the present invention to use water soluble sulfa drugs or water soluble salts thereof. The preferred sulfa drugs are sulfamonomethoxine, sulfadimethoxine, sulfadimidine and sulfachloropyridazine, or the pharmaceutically acceptable salts thereof such as the alkaline metal salts, especially the sodium salt.

The components of the composition may be mixed with any suitable carrier such as sugar, dextrin, dextrose, sodiumchloride, etc.

The compositions may be administered per se or in the form of tablets, capsules, ampules, suppositories, suspensions, solutions, etc.

The preferred ratio of trimethoprim to sulfa drug to phenoxyethanol in the composition of the present invention is 1:3-10:0.3-0.6.

For use in the treatment of bacterial infections in human beings, the composition of the invention is prepared in a suitable administration form by known methods, for example, by mixing with a suitable pharmaceutical binder, extender, carrier, emulsifier, solvent or the like.

For the treatment of bacterial infections in animals and birds, the composition is preferably introduced in the drinking water in an amount of about 0.4 g-1 g of the composition per liter of water.

DESCRIPTION OF THE PREFERRED EMBODIMENTS

The following examples are given to further illustrate the present invention. The scope of the invention is not, however, meant to be limited to the specific details of the examples.

EXAMPLE 1

The composition comprising the following ingredients was prepared by mixing:

| | |
|---|---|
| Sodium sulfachloropyridazine | 39.4 g |
| Trimethoprim | 7.8 g |
| Phenoxyethanol | 1.44 g |
| Sugar | 13.14 g |

EXAMPLE 2

The composition comprising the following ingredients was prepared by mixing:

| | |
|---|---|
| Sodium sulfachloropyridazine | 31.77 g |
| Trimethoprim | 5.355 g |
| Phenoxyethanol | 1.175 g |
| Dextrose up to | 100 g |

EXAMPLE 3

The composition comprising the following ingredients was prepared by mixing:

| | |
|---|---|
| Sodium sulfamonomethoxine | 31.77 g |
| Trimethoprim | 6.355 g |
| Phenoxyethanol | 1.2 g |
| Dextrose | 60.68 g |

EXAMPLE 4

The composition comprising the following ingredients was prepared by mixing:

| | |
|---|---|
| Sodium sulfadimethoxine | 63.54 g |

-continued

| | |
|---|---|
| Trimethoprim | 12.71 g |
| Phenoxyethanol | 6.35 g |
| Sodium Saccharin | 0.20 g |
| Dextrin | 17.20 g |

EXAMPLE 5

The composition comprising the following ingredients was prepared by mixing:

| | |
|---|---|
| Sodium sulfadimidine | 63.54 g |
| Trimethoprim | 12.71 g |
| Phenoxy ethanol | 3.2 g |
| Sodium Saccharin | 0.15 g |
| Sugar | 20.40 g |

The dosage in all the cases Examples 1-5 is: 0.5 g in 1 litre of water.

EXAMPLE 6

Nine-day old "Kabir" chick weighing 60–75 g were randomly divided into groups of 8 chicks per group and put into separate cages. All groups received food ad libitum. Water was rationed to 300 ml per day (with or without medication as indicated), during the four treatment days, and then ad. lib. All groups received in both experiments the treatment in the drinking water at the indicated concentration on day 0 (i.e., the day prior to the day of infection), on the date of infection (day 1), and on the two following days (days 2 and 3). The results are given in the following Tables:

TABLE I

| Group | Dose | Ave. Final wt. in gm. | ≠≠ dead/day ≠≠ | | | | | | | | | | | ≠≠ dead/ total | Autopsy Results Peri-card-itis | Peri-hepa-titis | Peri-toni-tis | ≠≠ cured total ≠≠ |
|---|---|---|---|---|---|---|---|---|---|---|---|---|---|---|---|---|---|---|
| | | | 0 | 1 | 2 | 3 | 4 | 5 | 6 | 7 | 8 | 9 | 10 | | | | | |
| 1 | 0.32 g/l | 131 | — | — | 1 | — | 2 | — | 1 | — | — | — | — | ⅜ | 1 | 1 | 1 | 2/8 |
| 2 | 0.50 g/l | 142 | — | — | — | — | — | — | — | — | — | — | — | 0/8 | 0 | 0 | 0 | 8/8 |
| 3 | 0.50 g/l | 150 | — | — | — | — | 1 | — | 1 | — | — | — | — | 2/8 | 1 1 sl. | 0 | 0 | 4/8 |
| 4 | 0.064 g/l | 107 | — | 2 | — | — | 1 | — | — | — | — | — | — | 4/8 | 2 sl. | 0 | 1 sl. | 2/8 |
| 5 | — | 125 | — | 3 | — | — | 1 | — | 1 | 1 | — | — | — | 6/8 | 1 | 1 | 1 | ⅛ |
| 6 | — | 149 | — | — | — | — | — | — | — | — | — | — | — | 0/8 | 0 | 0 | 0 | 8/8 |

In Table I the groups have the following meanings:
1. Sodium sulfachloropyridazine
2. Sodium sulfachloropyridazine + trimethoprim + phenoxyethanol
3. Sodium sulfachloropyridazine + trimethoprim
4. Trimethoprim
5. Infected untreated control group
6. Uninfected untreated control group.

TABLE II

| Composition | Total dead | Total ill | Total Completely Cured |
|---|---|---|---|
| 1 | 4 | 1 | 3 |
| 2 | 1 | 1 | 6 |
| 3 | 4 | 2 | 2 |
| 4 | 3 | 2 | 3 |
| 5 | 3 | 3 | 2 |
| 6 | 2 | 2 | 4 |
| 7 | 4 | 2 | 2 |
| 8 | 2 | 2 | 4 |
| 9 | 6 | 2 | — |
| 10 | — | — | 8 |

In Table II the compositions have the following meanings:
1. Sodium sulfachloropyridazine + trimethoprim
2. Sodium sulfachloropyridazine + trimethoprim + phenoxyethanol
3. Sodium sulfamonomethoxine + trimethoprim
4. Sodium sulfamonomethoxine + trimethoprim + phenoxyethanol
5. Sodium sulfadimethoxine + trimethoprim
6. Sodium sulfadimethoxine + trimethoprim + phenoxyethanol
7. Sodium sulfadimidine + trimethoprim
8. Sodium sulfadimidine + trimethoprim + phenoxyethanol
9. Infected untreated control group
10. Uninfected untreated control group.

In this experiment the alkali salts of the sulfa drugs were utilized. The dose was always 0.5 g of composition /l of water.

Further tests were carried out to evalute the effectiveness of the compositions of the invention. These tests are summarized in the table which follows.

Old crossed, light, chicks were held in a laboratory until day 10. The chicks were given free access to feed on a specially prepared mixture not containing any antibiotics, anticocidials, or vitamins, and water.

On day 10 the chicks were weighed, chicks weighing $60 \pm =$ grams were randomly divided into 20 groups of 8 chicks each and placed in special individual group cages, each cage with its own feed and water troughs.

All chicks were then given feed ad lib, and 300 ml of water containing the indicated medication.

On the following day all chicks were given an I.P. injection of 0.5 ml suspension of $2 \times 10^6$ organisms E.-coli $O_{78}$ in 5% mucin solution, (except for the control groups as indicated in the results table).

The chicks were also given another treatment with the medication as indicated.

Treatment was continued for 2 more days post infection day. The chicks were observed closely for 10 day post infection, all dead chicks were autopsied.

On the 11th day post inoculation, all chicks were weighed, sacrificed and autopsied.

The severity and presence or lack of infection in each chick was recorded according to the disease scoring key.

In the table, TMP stands for trimethoprim, SCP stands for sulfachloropyridazine and PhE stands for phenoxyethanol.

It should further be noted that the results "cured" and "slightly sick" should be considered as a single group, and "sick" and "dead" as another group.

While the invention has been illustrated with respect to particular compositions, it is apparent that variations and modifications of the invention can be made without departing from the spirit or scope of the invention.

3. Composition according to claim 1 wherein said sulfa drug is sulfachloropyridazine or its sodium salt.

4. Composition according to claim 3 wherein said sulfa drug is sodium sulfachloropyridazine.

5. Antibacterial pharmaceutical composition comprising drinking water and an antibacterial effective amount of the composition of claim 1.

| Group | Dose Mg/liter | | | Components ratio w/w | | | Therapy results on chicks | | | |
|---|---|---|---|---|---|---|---|---|---|---|
| | TMP | SCP | PhE | TMP | SCP | PhE | Cured | Sl. sick | sick | Dead |
| 1 | — | 300 | — | — | — | — | 0/8 | ⅛ | ⅜ | 4/8 |
| 2 | — | 1300 | — | — | — | — | ⅜ | ⅛ | ⅛ | ⅜ |
| 3 | 60 | — | — | — | — | — | ⅛ | ⅛ | 2/8 | 4/8 |
| 4 | — | — | 18 | — | — | — | 0/8 | ⅛ | ⅜ | 4/8 |
| 5 | — | 300 | 18 | — | 16.6 | .1 | ⅛ | — | 4/8 | ⅜ |
| 6 | 60 | — | 18 | 1 | — | 0.3 | 2/8 | — | 4/8 | 2/8 |
| 7 | 100 | 300 | — | 1 | 3 | — | 4/7 | 1/7 | 1/7 | 1/7 |
| 8 | 75 | 300 | — | 1 | 4 | — | ⅜ | ⅛ | ⅛ | ⅛ |
| 9 | 60 | 300 | — | 1 | 5 | — | ⅜ | 2/8 | ⅛ | 2/8 |
| 10 | 100 | 300 | 18 | 1 | 3 | 0.18 | 6/7 | — | — | 1/7 |
| 11 | 75 | 300 | 18 | 1 | 4 | 0.24 | ⅞ | ⅛ | — | — |
| 12 | 60 | 300 | 30 | 1 | 5 | 0.5 | ⅞ | ⅛ | — | — |
| 13 | 60 | 300 | 18 | 1 | 5 | 0.3 | 8/8 | — | — | — |
| 14 | 30 | 300 | 18 | 1 | 10 | 0.6 | ⅝ | ⅜ | — | — |
| 15 | 60 | 300 | 11.0 | 1 | 5 | 0.18 | ⅝ | ⅛ | 2/8 | 0/8 |
| 16 | Infected untreated control IUC | | | | | | 0/8 | 0/8 | ⅜ | ⅝ |
| 17 | Uninfected untreated control UUC | | | | | | — | — | — | — |

What is claimed is:

1. Antibacterial pharmaceutical composition, comprising synergistically effective amounts of phenoxyethanol, trimethoprim, and as a sulfa drug, sulfachloropyridazine or pharmaceutically acceptable salts thereof, in an antibacterial effective amount,
wherein the ratio of said trimethoprim to said sulfa drug to said phenoxyethanol is about 1:3–10:0.1–0.6.

2. Composition according to claim 1, said composition being distributed in a pharmaceutically acceptable carrier suitable for internal administration.

6. Method of treating bacterial infections, which comprises administering to a patient having a bacterial infection an antibacterial effective amount of the composition of claim 1.

7. Antibacterial pharmaceutical composition, comprising synergistically effective amounts of phenoxyethanol, trimethoprim, and as a sulfa drug, sulfachloropyridazine or pharmaceutically acceptable salts thereof, in an antibacterial effective amount,
wherein the ratio of said trimethoprim to said sulfa drug to said phenoxyethanol is 1:3–10:0.3–0.6.

* * * * *